(12) United States Patent
Janssen et al.

(10) Patent No.: US 8,734,530 B2
(45) Date of Patent: May 27, 2014

(54) COLORANTS IN FOAM FORM

(71) Applicant: Henkel AG & Co. KGaA, Duesseldorf (DE)

(72) Inventors: Frank Janssen, Cologne (DE); Jurgen Schopgens, Schwalmtal (DE); Sabine Babiel, Moers (DE); Armin Wadle, Erkrath (DE); Udo Erkens, Neuss-Grimlinghausen (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

(21) Appl. No.: 13/740,344

(22) Filed: Jan. 14, 2013

(65) Prior Publication Data

US 2013/0125917 A1    May 23, 2013

Related U.S. Application Data

(63) Continuation of application No. PCT/EP2011/058815, filed on May 30, 2011.

(30) Foreign Application Priority Data

Jul. 15, 2010   (DE) .......................... 10 2010 031 368

(51) Int. Cl.

| | | |
|---|---|---|
| *A61Q 5/10* | (2006.01) | |
| *C07D 209/04* | (2006.01) | |
| *A61Q 5/06* | (2006.01) | |
| *A61K 8/04* | (2006.01) | |
| *A61K 8/64* | (2006.01) | |
| *A61K 8/49* | (2006.01) | |
| *C07D 209/00* | (2006.01) | |
| *C07D 209/08* | (2006.01) | |
| *C09B 29/40* | (2006.01) | |

(52) U.S. Cl.
CPC *A61Q 5/10* (2013.01); *A61Q 5/065* (2013.01); *A61K 8/046* (2013.01); *A61K 8/64* (2013.01); *A61K 8/492* (2013.01); *C07D 209/00* (2013.01); *C07D 209/04* (2013.01); *C07D 209/08* (2013.01); *C09B 29/3613* (2013.01)

USPC ......... 8/405; 8/426; 8/574; 548/490; 548/491

(58) Field of Classification Search
CPC ......... A61K 8/046; A61K 8/492; A61K 8/64; A61Q 5/065; A61Q 5/10; C07D 209/00; C07D 209/04; C07D 209/08; C09B 29/3613
USPC .............. 8/405, 406, 409, 574, 611; 548/290, 548/291
See application file for complete search history.

(56) References Cited

U.S. PATENT DOCUMENTS

| | | |
|---|---|---|
| 4,900,326 A | 2/1990 | Grollier |
| 6,702,863 B1 | 3/2004 | Onuki |
| 6,818,023 B2 * | 11/2004 | Hoeffkes et al. .................. 8/409 |

FOREIGN PATENT DOCUMENTS

| | | |
|---|---|---|
| DE | 102004062428 A1 | 7/2006 |
| EP | 1321128 A2 | 6/2003 |
| EP | 1342465 A2 | 9/2003 |
| FR | 2599970 A1 | 12/1987 |

OTHER PUBLICATIONS

STIC Search Report dated Mar. 13, 2013.*
European Patent Office, International Searching Authority "International Search Report" mailed Jan. 16, 2013; International Application No. PCT/EP2011/058815, filed May 30, 2011.
Schrader, Karlheinz, "Very Core Basics and Recipes of Cosmetics", 1989.

* cited by examiner

*Primary Examiner* — Eisa Elhilo
(74) *Attorney, Agent, or Firm* — Ingrassia Fisher & Lorenz, P.C.

(57) ABSTRACT

An agent in foam form for coloring keratin-containing fibers, in particular human hair, under induction by atmospheric oxygen and methods for coloring keratin-containing fibers using such agent is provided. In an embodiment, the agent comprises, in a cosmetically acceptable carrier, at an alkaline pH of 8 to 10.5, (a) as a color-forming component in the form of a dye precursor of a nature-analogous dye an indole and/or indoline derivative, (b) an alkalizing agent, and (c) a propellant, the agent containing no additional oxidizing agent for the color-forming components.

18 Claims, No Drawings

COLORANTS IN FOAM FORM

CROSS-REFERENCE TO RELATED APPLICATION

This is a continuation of International Application No. PCT/EP2011/058815, filed May 30, 2011, which was published under PCT Article 21(2) and which claims priority to German Application No. 102010031368.8, filed Jul. 15, 2010, which are all hereby incorporated in their entirety by reference.

TECHNICAL FIELD

The technical field relates to agents in foam form for coloring keratin-containing fibers and the use thereof. The agents contain a dye precursor for a nature-analogous dye selected from the group of indole or indoline derivatives, a propellant and an alkalizing agent and are free from additional oxidizing agents.

BACKGROUND

The person skilled in the art is familiar with various coloring systems for the provision of color-changing cosmetic agents, in particular for the skin or keratin-containing fibers such as human hair for example, depending on the requirements of the coloring process. In addition to oxidation coloring agents for permanent intense colors with corresponding fastness properties and coloring or tinting agents for temporary colors which contain substantive dyes as the coloring component, coloring agents are known which contain as dyes precursors of the natural hair dye melanin, from which nature-analogous dyes are developed through oxidative processes in the hair.

These colorings can take place under oxidation with atmospheric oxygen as the sole oxidizing agent, such that no further additional oxidizing agents need to be used. Such colorings are therefore particularly gentle on the hair structure. With repeated use in particular, the agents make it possible to restore the natural hair color of people with gray hair. However, the coloring capacities of the agents, with oxidization under atmospheric oxygen in particular, are in many cases unsatisfactory, requiring long contact periods or frequent repetitions of the coloring process.

Hair coloring agents based on dye precursors of the indole or indoline type are known from the publication EP-B1-1 098 627, which additionally contain an amino acid or an oligopeptide to improve colorings on gray hair. On blonde hair the colorings achieved all have an undesired red or blue tinge.

There is therefore a need for effective coloring agents based on nature-analogous dye precursors that form intense colorings even with atmospheric oxygen as the sole oxidizing agent. There also is a need for colorings that turn out with no undesired reddish, bluish or violet color shifts. In addition, there is a need for colorings that are long-lasting and develop quickly. Another object is moreover a reduction in the contact period and improved application of the hair color for the user. Furthermore, other objects, desirable features and characteristics will become apparent from the subsequent summary and detailed description, and the appended claims, taken in conjunction with the accompanying drawings and this background.

SUMMARY

An agent in foam form for coloring keratin-containing fibers, in particular human hair, under induction by atmospheric oxygen and methods for coloring keratin-containing fibers using such agent is provided. In accordance with an exemplary embodiment, an agent in foam form for coloring keratin-containing fibers, in particular human hair, under induction by atmospheric oxygen, is provided. The agent comprises, in a cosmetically acceptable carrier, at an alkaline pH of 8 to 10.5:

(a) as a color-forming component in the form of a dye precursor of a nature-analogous dye an indole and/or indoline derivative of formula (I),

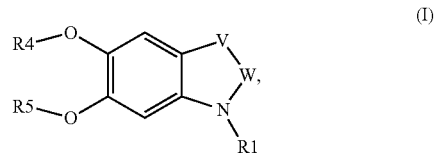

in which independently of one another
$R^1$ denotes hydrogen, a $C_1$-$C_4$ alkyl group or a $C_1$-$C_4$ hydroxyalkyl group,
V denotes $CHR^3$ and W denotes $CHR^2$, such that the bond between V and W corresponds to a single bond,
or V denotes $CR^3$ and W denotes $CR^2$, such that the bond between V and W corresponds to a double bond, wherein in each case
—$R^2$ denotes hydrogen or a —COOH group, in which the —COOH group can also be present as a salt with a physiologically tolerable cation,
—$R^3$ denotes hydrogen or a $C_1$-$C_4$ alkyl group,
$R^4$ and $R^5$ independently of one another denote hydrogen, a $C_1$-$C_4$ alkyl group or a —CO—$R^6$ group, in which $R^6$ denotes a $C_1$-$C_4$ alkyl group,
and/or one of the physiologically tolerable salts thereof with an organic or inorganic acid,
(b) an alkalizing agent, and
(c) a propellant,
wherein no additional oxidizing agent is included for the color-forming components.

In accordance with another exemplary embodiment, a method for coloring keratin-containing fibers is provided. The method comprises applying an agent to the keratin-containing fibers. The agent comprises, in a cosmetically acceptable carrier, at an alkaline pH of 8 to 10.5:

(a) as a color-forming component in the form of a dye precursor of a nature-analogous dye an indole and/or indoline derivative of formula (I),

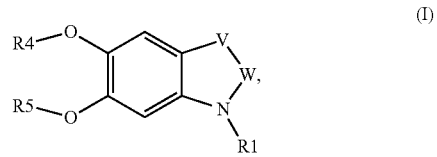

in which independently of one another
$R^1$ denotes hydrogen, a $C_1$-$C_4$ alkyl group or a $C_1$-$C_4$ hydroxyalkyl group,
V denotes $CHR^3$ and W denotes $CHR^2$, such that the bond between V and W corresponds to a single bond,
or V denotes $CR^3$ and W denotes $CR^2$, such that the bond between V and W corresponds to a double bond, wherein in each case —$R^2$ denotes hydrogen or a —COOH group, in which the —COOH group can also be present as a salt with a physiologically tolerable cation, —$R^3$ denotes hydrogen or a $C_1$-$C_4$ alkyl group, $R^4$ and $R^5$ independently of one another denote hydrogen, a $C_1$-$C_4$ alkyl group or a —CO—$R^6$ group, in which $R^6$ denotes a $C_1$-$C_4$ alkyl group, and/or one of the physiologically tolerable salts thereof with an organic or inorganic acid, (b) an alkalizing agent, and (c) a propellant, wherein no additional oxidizing agent is included for the color-forming components. The agent is allowed to remain on the keratin-containing fibers for a contact period and the agent is rinsed from the keratin-containing fibers after the contact period.

DETAILED DESCRIPTION

In its investigations the applicant found that the color intensity of nature-analogous colorings can be significantly increased if the coloring agent is applied as a foam. The application was markedly improved by this means as compared with other product forms such as creams or gels. The contact period for such coloring foams could likewise be markedly reduced with no adverse effects on the coloring result.

An exemplary embodiment therefore firstly provides agents in foam form for coloring keratin-containing fibers, in particular human hair, under induction by atmospheric oxygen, the agents containing, in a cosmetically acceptable carrier, at an alkaline pH of about 8.8 to about 10.5

(a) as a color-forming component in the form of a dye precursor of a nature-analogous dye an indole and/or indoline derivative of formula (I),

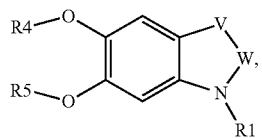

in which independently of one another $R^1$ denotes hydrogen, a $C_1$-$C_4$ alkyl group or a $C_1$-$C_4$ hydroxyalkyl group, V denotes $CHR^3$ and W denotes $CHR^2$, such that the bond between V and W corresponds to a single bond, or V denotes $CR^3$ and W denotes $CR^2$, such that the bond between V and W corresponds to a double bond, wherein in each case —$R^2$ denotes hydrogen or a —COOH group, in which the —COOH group can also be present as a salt with a physiologically tolerable cation, —$R^3$ denotes hydrogen or a $C_1$-$C_4$ alkyl group, $R^4$ and $R^5$ independently of one another denote hydrogen, a $C_1$-$C_4$ alkyl group or a —CO—$R^6$ group, in which $R^6$ denotes a $C_1$-$C_4$ alkyl group, and/or one of the physiologically tolerable salts thereof with an organic or inorganic acid, (b) an alkalizing agent, and (c) a propellant, and wherein they contain no additional oxidizing agent for the color-forming components.

According to the various embodiments the term keratin-containing fibers is understood here to mean fur, wool, feathers and in particular human hair. Although the coloring agents according to the various embodiments are primarily suitable for coloring keratinic fibers, there is in principle nothing to preclude a use in other areas of coloring too, provided the technical object underlying the various embodiments is achieved.

Other than atmospheric oxygen, with which they come into contact during preparation, storage or use, the agents contain no further additional oxidizing agent, but in particular no peroxo compounds such as hydrogen peroxide, persulfates, peroxomonosulfates, perborates, chlorites, hypochlorites or peroxide salts.

As additional oxidizing agents the agents according to an embodiment also contain in particular no enzymes having an oxidative effect, such as peroxidases, laccases or 2-electron oxidoreductases in combination with the substrates specific thereto, such as for example pyranose oxidase and for example D-glucose or galactose, glucose oxidase and D-glucose, glycerol oxidase and glycerol, pyruvate oxidase and benzotartaric acid or salts thereof, alcohol oxidase and alcohol (MeOH, EtOH), lactate oxidase and lactic acid and salts thereof, tyrosinase oxidase and tyrosine, uricase and uric acid or salts thereof and choline oxidase and choline as well as amino acid oxidase and corresponding amino acids.

A cosmetically acceptable carrier is understood to be an otherwise conventional carrier of agents for coloring human hair. The agents according to an embodiment preferably contain the components in a suitable aqueous, alcoholic or aqueous-alcoholic carrier.

As used herein, aqueous-alcoholic solutions are understood to be aqueous solutions containing about 3 to about 70 weight percent (wt. %) of a $C_1$ to $C_4$ alcohol, in particular ethanol or isopropanol. The agents according to an embodiment can additionally contain further organic solvents, such as for example methoxybutanol, benzyl alcohol, ethyl diglycol or 1,2-propylene glycol. All water-soluble organic solvents are preferred here. Cosmetic carriers that are preferred according to an embodiment contain a water-soluble solvent, selected in particular from ethanol, isopropanol, ethylene glycol, 1,2-propylene glycol, 1,3-propylene glycol, 1,2-butylene glycol, 1,3-butylene glycol and 1,4-butylene glycol. The solvent or solvents are preferably included in a total amount from about 3 to about 50 wt. %, preferably about 5 to about 40 wt. %, relative in each case to the total weight of the ready-to-use agents.

As a first substantial ingredient the agents according to an embodiment contain as a color-forming component (a) in the form of a dye precursor of a nature-analogous dye an indole and/or indoline derivative of formula (I).

Particularly suitable indole derivatives of formula (I) according to an embodiment are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid and/or one of the physiologically tolerable salts thereof with an organic or inorganic acid.

Derivatives of 5,6-dihydroxyindoline are particularly suitable as precursors of nature-analogous hair dyes. A first embodiment therefore has the characterizing feature that the indoline derivative (a) is selected from derivatives of 5,6-dihydroxyindoline of formula (Ia)

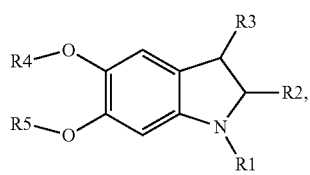

(Ia)

in which independently of one another

R[1] denotes hydrogen, a $C_1$-$C_4$ alkyl group or a $C_1$-$C_4$ hydroxyalkyl group, R[2] denotes hydrogen or a —COOH group, in which the —COOH group can also be present as a salt with a physiologically tolerable cation, R[3] denotes hydrogen or a $C_1$-$C_4$ alkyl group, R[4] and R[5] independently of one another denote hydrogen, a $C_1$-$C_4$ alkyl group or a —CO—R[6] group, in which R[6] denotes a $C_1$-$C_4$ alkyl group, and/or one of the physiologically tolerable salts thereof with an organic or inorganic acid.

Another embodiment has the characterizing feature that the indoline derivative of feature (a) is selected from the group formed from 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline and 5,6-dihydroxyindoline-2-carboxylic acid and/or physiologically tolerable salts thereof with an organic or inorganic acid.

In particular, 5,6-dihydroxyindoline and/or the physiologically tolerable salts thereof with an organic or inorganic acid is particularly preferred.

In the coloring agents according to an embodiment the indoline and indole derivatives can be used both as free bases and in the form of their physiologically tolerable salts with inorganic or organic acids, for example hydrochlorides, sulfates and hydrobromides.

The precursors of nature-analogous dyes are preferably contained in the agents according to an embodiment in an amount from about 0.01 to about 10 wt. %, in particular from about 0.1 to about 5 wt. %, preferably about 0.1 to about 2.0 wt. % and particularly preferably about 0.6 to about 1.2 wt. %, relative in each case to the total weight of the ready-to-use agent.

The agents according to an embodiment are in foam form. As used herein, a foam is defined as a structure comprising gas-filled spherical or polyhedral cells that are delimited by liquid cell walls. This leads to a large surface area and hence to an enlarged area of contact between the agent and its environment. Furthermore, an agent in foam form can be distributed particularly uniformly over the application area.

The agent contains one or more propellants to form the foam. Propellants are understood to be substances that are themselves already in gas form or are capable of developing gas. Preferred propellants are selected from hydrocarbons, halogenated hydrocarbons, in particular chlorofluorocarbons and fluorocarbons, volatile ethers, in particular dimethyl ethers, nitrogen oxides, in particular $N_2O$, carbon dioxide and compressed air. Particularly preferred propellants are alkanes having 3 to 5 carbon atoms.

A further embodiment is therefore an agent having the characterizing feature that the propellant (c) is selected from the group formed from propane, n-butane, i-butane, pentane and mixtures of these compounds.

The agents according to an embodiment contain the propellants in an amount of up to about 20 wt. %, in particular up to about 15 wt. % and particularly preferably up to about 10 wt. %, relative in each case to the total weight of the ready-to-use agent.

The agent according to an embodiment has a basic pH in the range from about 8 to about 10.5. Agents that are preferred have a pH from about 8.8 to about 10.5, particularly preferably about 9.4 to about 9.9.

The alkaline pH of the agents according to an embodiment is necessary inter alia to open up the hair structure to allow the nature-analogous dye precursors to enter and to ensure they penetrate into the interior of the hair. The agent therefore contains as a further substantial ingredient an alkalizing agent to adjust the pH.

The person skilled in the art is familiar with a large number of different alkalizing agents for adjusting the pH of cosmetic preparations, in particular ammonia, organic alkalizing agents such as amines, alkanol amines or basic amino acids, and inorganic alkalizing agents such as hydroxides, metasilicates, carbonates, phosphates and hydrogen phosphates of ammonium, alkali metals and alkaline-earth metals.

Ammonia is known for being able to make an additional contribution to color depth. It can however also lead to undesired color shifts. For the user, however, such a coloring agent has the disadvantage that in addition to causing additional damage to the hair, ammonia can also lead to irritation of the eyes or scalp, which can give rise to sensitization or even to allergic reactions. A further disadvantage consists in the fact that because of its relative volatility, ammonia gives the agent a strong odor which is perceived as being objectionable and which in the worst-case scenario can also lead to irritation of the scalp and mucous membranes, such as nasal or ocular mucous membranes.

As the volatility of ammonia in an agent in foam form has a particularly strong effect on odor formation because of the enlarged surface area, it is particularly desirable to provide agents which still lead to very good coloring results but dispense with the use of ammonia. It is therefore particularly advantageous if the agent is low in ammonia or preferably ammonia-free.

The terms "low in ammonia" or "ammonia-free" as used herein relate to the amount of ammonia added to the agent, wherein the ammonia can be added both as an aqueous, alcoholic, aqueous-alcoholic or other solution and by the introduction of ammonia gas or by the addition of liquefied ammonia. The terms "ammonia-free" or "low in ammonia" as used herein relate in particular not to ammonia released in the agent contemplated herein, which is formed by deprotonation of ammonium cations added as a salt.

Preferred low-ammonia agents contain less than 0.5 wt. % about, in particular less than 0. about 1 wt. % and most particularly preferably less than about 0.05 wt. % of added ammonia, relative in each case to the total weight of the application preparation. Ammonia-free within the meaning of the agent refers to agents to which no ammonia has been added by one of the methods described above. Such agents are most particularly preferred.

It has been found that the agent according to an embodiment contains inorganic alkalizing agents as a particularly suitable alkalizing agent (b). Carbonates and hydroxides of alkali metals are particularly preferred here. A particular embodiment is therefore an agent having the characterizing feature that it contains as the alkalizing agent (b) an inorganic alkalizing agent selected from the group formed from sodium hydroxide, potassium hydroxide, sodium carbonate and potassium carbonate.

The agents according to an embodiment contain the alkalizing agents in an adequate amount to establish the desired pH. Preferred agents have the characterizing feature that they contain the inorganic alkalizing agent(s), selected from sodium hydroxide, potassium hydroxide, sodium carbonate and potassium carbonate, in an amount from about 0.1 to about 5 wt. %, preferably about 0.2 to about 1 wt. %.

The agents according to an embodiment can furthermore additionally contain a fatty alcohol. It has been found that for application reasons and/or in the interests of optimum color development, the proportion of fatty alcohols in the agent according to an embodiment should not be too high, and in particular should not exceed about 2 wt. %.

A further embodiment is therefore an agent having the characterizing feature that it additionally contains a fatty alcohol in an amount from 0 to about 2 wt. %, preferably about 0.1 to about 2 wt. % and in particular preferably about 0.2 to about 1.5 wt. %, relative in each case to the total weight of the ready-to-use agent.

A fatty alcohol is understood herein to be a non-cyclic monohydroxy hydrocarbon having 8 to 24 carbon atoms. These are preferably long-chain, optionally branched compounds, which are saturated or can have one to four C—C double bonds.

Examples are 1-octanol, 6-methylheptan-1-ol, 3,3-dimethylhexan-1-ol, 3,5-dimethylhexan-1-ol, 4,5-dimethylhexan-1-ol, 3-methylheptan-1-ol, 5-methylheptan-1-ol (isooctanols) and 2-ethylhexan-1-ol (ethylhexyl alcohol), 1-decanol, 1-dodecanol (lauryl alcohol), 1-tetradecanol (myristyl alcohol), 1-hexadecanol (cetyl alcohol), 1-octadecanol (stearyl alcohol) and 16-methylheptadecan-1-ol (isostearyl alcohol), palmitoleyl alcohol (C16:1; 9Z), oleyl alcohol (C18:1; 9Z), elaidinyl alcohol (C18:1; 9E), eicosenyl alcohol (C20:1; 11Z) and fatty alcohol cuts from natural sources, such as lanolin alcohol, coconut fatty alcohol and tallow fatty alcohol, and from synthetic sources, such as cetearyl alcohol. Cetyl alcohol, stearyl alcohol and tallow fatty alcohol, cetearyl alcohol and coconut fatty alcohol are particularly preferred.

In many cases the coloring agents contain a surfactant, with both anionic and zwitterionic, ampholytic, non-ionic and cationic surfactants being suitable in principle. It has proved advantageous in many cases, however, to select the surfactants from anionic, cationic or non-ionic surfactants. The foam stability of the agent in particular can be influenced by adding surfactants.

A further embodiment is therefore an agent having the characterizing feature that it additionally contains a surfactant in an amount from about 0.1 to about 5 wt. %, preferably about 0.2 to about 3 wt. %, relative in each case to the total weight of the ready-to-use agent.

All anionic surface-active substances that are suitable for use on the human body are suitable as anionic surfactants in preparations contemplated herein. Examples of suitable anionic surfactants, each in the form of the sodium, potassium and ammonium salts as well as the mono-, di- and trialkanolammonium salts having 2 or 3 C atoms in the alkanol group, are anionic alkyl oligoglycosides or anionic alkenyl oligoglycoside derivatives, selected from alkyl and/or alkenyl oligoglycoside carboxylates, sulfates, phosphates and/or isethionates, linear fatty acids having 10 to 22 C atoms (soaps), ether carboxylic acids of the formula R—O—($CH_2$—$CH_2O$)$_x$—$CH_2$—COOH, in which R is a linear alkyl group having 10 to 22 C atoms and x=0 or 1 to 16, acyl sarcosides having 10 to 18 C atoms in the acyl group, acyl taurides having 10 to 18 C atoms in the acyl group, acyl isethionates having 10 to 18 C atoms in the acyl group, sulfosuccinic acid mono- and dialkyl esters having 8 to 18 C atoms in the alkyl group and sulfosuccinic acid monoalkyl polyoxyethyl esters having 8 to 18 C atoms in the alkyl group and 1 to 6 oxyethyl groups, linear alkane sulfonates having 12 to 18 C atoms, linear alpha-olefin sulfonates having 12 to 18 C atoms, alpha-sulfo fatty acid methyl esters of fatty acids having 12 to 18 C atoms, alkyl sulfates and alkyl polyglycol ether sulfates of the formula R—O($CH_2$—$CH_2O$)$_x$—$SO_3H$, in which R is a preferably linear alkyl group having 10 to 18 C atoms and x=0 or 1 to 12, sulfonates of unsaturated fatty acids having 12 to 24 C atoms and 1 to 6 double bonds, esters of tartaric acid and citric acid with alcohols that are addition products of around 2 to 15 molecules of ethylene oxide and/or propylene oxide with fatty alcohols having 8 to 22 C atoms.

Preferred anionic surfactants are alkyl sulfates, alkyl polyglycol ether sulfates and ether carboxylic acids having 10 to 18 C atoms in the alkyl group and up to 12 glycol ether groups in the molecule.

Non-ionic surfactants contain as a hydrophilic group a polyol group, a polyalkylene glycol ether group or a combination of a polyol and polyglycol ether group, for example. Such compounds are for example addition products of 2 to 30 mol of ethylene oxide and/or 0 to 5 mol of propylene oxide with linear fatty alcohols having 8 to 22 C atoms, with fatty acids having 12 to 22 C atoms and with alkyl phenols having 8 to 15 C atoms in the alkyl group, $C_{12}$-$C_{22}$ fatty acid monoesters and diesters of addition products of 1 to 30 mol of ethylene oxide with glycerol, $C_8$-$C_{22}$ alkyl mono- and oligoglycosides and ethoxylated analogs thereof, and addition products of 5 to 60 mol of ethylene oxide with castor oil and hydrogenated castor oil.

Preferred non-ionic surfactants are the addition products of 2 to 30 mol of ethylene oxide with linear fatty alcohols having 12 to 20 C atoms, such as for example Laureth-2, Laureth-10, Ceteareth-12, Ceteareth-20, Ceteareth-25, Oleth-12, and alkyl mono- and oligoglycosides, such as lauryl glucosides, stearyl glucosides or cocoyl glucosides.

Cationic surfactants of the quaternary ammonium compound, esterquat and amidoamine type in particular can be used herein. Preferred quaternary ammonium compounds are ammonium halides, in particular chlorides and bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI names Quaternium-27 and Quaternium-83. Esterquats are known substances containing both an ester function and a quaternary ammonium group as a structural element. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines, such as N,N-bis-(2-palmitoyloxyethyl)dimethyl ammonium chloride. The alkylamidoamines are conventionally produced by amidation of natural or synthetic fatty acids and fatty acid cuts with dialkyl amino amines. A particularly suitable compound for use herein is stearamidopropyl dimethylamine. Other cationic surfactants which can be used according to an embodiment are the quaternized protein hydrolysates. Likewise suitable are cationic silicone oils, such as for example the commercially available products Q2-7224 (manufacturer: Dow Corning; a stabilized trimethylsilyl amodimethicone), Dow Corning 929 Emulsion (containing a hydroxyl-amino-modified silicone, which is also known as amodimethicone), SM-2059 (manufacturer: General Electric), SLM-55067 (manufacturer: Wacker) as well as Abil®-Quat 3270 and 3272 (manufacturer: Th. Goldschmidt; diquaternary polydimethylsiloxanes, Quaternium-80). An example of a quaternary sugar derivative that can be used as a cationic surfactant is the commercial product Glucquat®100, INCI name Lauryl Methyl Gluceth-10 Hydroxypropyl Dimonium Chloride.

Zwitterionic surfactants can moreover be used, in particular as co-surfactants. Surface-active compounds classed as zwitterionic surfactants are those bearing a quaternary ammonium group and a —COO$^{(-)}$ or —SO$_3$$^{(-)}$ group in the molecule. Particularly suitable zwitterionic surfactants are the betaines such as N-alkyl-N,N-dimethylammonium glycinates, for example cocoalkyl dimethylammonium glycinate, N-acyl aminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

Likewise suitable in particular as co-surfactants are ampholytic surfactants. Ampholytic surfactants are understood to be surface-active compounds that in addition to a $C_8$-$C_{18}$ alkyl or acyl group contain a free amino group and a —COOH or —SO$_3$H group in the molecule and are capable of forming internal salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids, each having approximately 8 to 18 C atoms in the alkyl group. Particularly preferred ampholytic surfactants are N-cocoalkyl aminopropionate, cocoacylaminoethyl aminopropionate and $C_{12}$-$C_{18}$ acyl sarcosine.

The agents according to another embodiment can additionally encompass oxidation dye precursors of the developer type, which in turn are preferably included in an amount from about 0.01 to about 5 wt. %, in particular from about 0.1 to about 3 wt. %, relative in each case to the weight of the ready-to-use coloring agent.

Preferred developer components are chosen from p-phenylene diamine, p-toluoylene diamine, 2-(β-hydroxyethyl)-p-phenylene diamine, 2-(α,β-dihydroxyethyl)-p-phenylene diamine, N,N-bis-(β-hydroxyethyl)-p-phenylene diamine, N-(4-amino-3-methylphenyl)-N-[3-(1H-imidazol-1-yl)propyl]amine, N,N'-bis-(β-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(α,β-dihydroxyethyl)phenol and 4-amino-2-(diethylaminomethyl)phenol, 4,5-diamino-1-(β-hydroxyethyl)pyrazole, 2,4,5,6-tetraminopyrimidine, 4-hydroxy-2,5,6-triaminopyrimidine, 2-hydroxy-4,5,6-triaminopyrimidine, as well as the physiologically tolerable salts thereof, and mixtures thereof.

In the context of oxidative dyeing, coupler components develop no significant color on their own but always need the presence of developer components. It is therefore preferable according to an embodiment that with the use of at least one developer component at least one coupler component is additionally used.

Preferred coupler components according to an embodiment are selected from m-aminophenol, 5-amino-2-methylphenol, 3-amino-2-chloro-6-methylphenol, 2-hydroxy-4-aminophenoxyethanol, 5-amino-4-chloro-2-methylphenol, 5-(2'-hydroxyethyl)amino-2-methylphenol, 2,4-dichloro-3-aminophenol, o-aminophenol, m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically tolerable salts thereof.

The coupler components are preferably used in an amount from about 0.005 to about 20 wt. %, preferably about 0.1 to about 5 wt. %, relative in each case to the ready-to-use oxidation coloring agent. Developer components and coupler components are generally used in approximately molar amounts to one another. Even if the molar use has proved convenient, a certain excess of individual oxidation dye precursors is not disadvantageous, such that developer components and coupler components can be in a molar ratio of about 1:0.5 to about 1:3, in particular about 1:1 to about 1:2.

In addition to the compounds, the coloring agents can contain in a further embodiment one or more substantive dyes for tinting purposes. Substantive dyes are conventionally nitrophenylene diamines, nitroaminophenols, azo dyes, anthraquinones or indophenols. Preferred substantive dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1 and Acid Black 52 as well as 1,4-diamino-2-nitrobenzene, 2-amino-4-nitrophenol, 1,4-bis-(β-hydroxyethyl)-amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitro-diphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene. The agents according to an embodiment can furthermore contain a cationic substantive dye. Cationic triphenylmethane dyes are preferred, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes containing a heterocyclic compound having a quaternary nitrogen atom, such as for example Basic Yellow 87, Basic Orange 31 and Basic Red 51. The cationic substantive dyes that are sold under the Arianor® brand are likewise most particularly preferred cationic substantive dyes according to an embodiment. The agents according to this embodiment preferably contain the substantive dyes in an amount from about 0.01 to about 20 wt. %, relative to the total coloring agent.

The preparations can furthermore also contain naturally occurring dyes, such as are contained for example in henna red, henna neutral, henna black, chamomile flowers, sandalwood, black tea, alder buckthorn bark, sage, logwood, madder root, catechu and alkanet root.

The coloring agents according to an embodiment can moreover contain further active ingredients, auxiliary substances and additives, such as for example

- cationic and/or amphoteric polymers such as Polyquaternium-2, Polyquaternium-4, Polyquaternium-6, Polyquaternium-7, Polyquaternium-10, Polyquaternium-11, Polyquaternium-16, Polyquaternium-17, Polyquaternium-18, Polyquaternium-22, Polyquaternium-24, Polyquaternium-27, Polyquaternium-28, Polyquaternium-32, Polyquaternium-37, Polyquaternium-39, Polyquaternium-44, Polyquaternium-46, Polyquaternium-55, Polyquaternium-59, Polyquaternium-67, Polyquaternium-68, Polyquaternium-69, Polyquaternium-87;
- non-ionic polymers such as vinyl pyrrolidinone/vinyl acrylate copolymers, polyvinyl pyrrolidinone and vinyl pyrrolidinone/vinyl acetate copolymers and polysiloxanes,
- anionic polymers such as for example polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers,
- amphiphilic polymers, such as the polymers corresponding to the INCI names: Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer,
- thickening agents such as agar-agar, guar gum, alginates, xanthan gum, gum arabic, karaya gum, carob seed meal, linseed gums, dextrans, cellulose derivatives, for example methyl cellulose, hydroxyalkyl cellulose and carboxymethyl cellulose, starch fractions and derivatives such as amylose, amylopectin and dextrins, clays such as for example bentonite or fully synthetic hydrocolloids such as for example polyvinyl alcohol,
- texturizing agents such as maleic acid and lactic acid,
- hair-conditioning compounds such as phospholipids, soy lecithin, egg lecithin and cephalins,
- protein hydrolysates, in particular elastin, collagen, keratin, milk protein, soy protein and wheat protein hydrolysates, condensation products thereof with fatty acids and quaternized protein hydrolysates,
- perfume oils, dimethyl isosorbide and cyclodextrins,
- active ingredients to improve the fiber structure, in particular mono-, di- and oligosaccharides such as for example glucose, galactose, fructose, fruit sugar and lactose,
- defoaming agents such as silicones,
- dyes to color the agent,
- anti-dandruff active ingredients such as piroctone olamine, zinc omadine and climbazole,
- light stabilizers, in particular derivatized benzophenones, cinnamic acid derivatives and triazines,
- active ingredients such as allantoin, pyrrolidone carboxylic acids and salts thereof and bisabolol,
- vitamins, provitamins and vitamin precursors, in particular those from groups A, $B_3$, $B_5$, $B_6$, C, E, F and H,
- plant extracts,
- cholesterol,
- consistency modifiers such as sugar esters, polyol esters or polyol alkyl ethers,
- fats and waxes such as beeswax, montan wax and paraffins,
- fatty acid alkanol amides,
- complexing agents such as EDTA, NTA, β-alanine diacetic acid and phosphonic acids, in particular etidronic acid,
- swelling and penetrating substances such as glycerol, propylene glycol monoethyl ether, carbonates, hydrogen carbonates, guanidines, ureas as well as primary, secondary and tertiary phosphates,
- opacifiers such as latex, styrene/PVP and styrene/acrylamide copolymers,
- pearlescent agents such as ethylene glycol mono- and distearate as well as PEG-3 distearate,
- pigments,
- stabilizing agents for hydrogen peroxide and other oxidizing agents.

With regard to further optional components and to the amounts of these components used, reference is expressly made to the relevant manuals known to the person skilled in the art, for example Kh. Schrader, Grundlagen and Rezepturen der Kosmetika, $2^{nd}$ Edition, Hüthig Buch Verlag, Heidelberg, 1989.

The application temperatures can be in a range between about 15 and about 40° C. After a contact period of generally about 2 to about 45 minutes, preferably about 5 to about 20 minutes, the hair coloring agent is removed by rinsing the hair to be dyed.

To gradually adjust gray hair to a test subject's original natural hair color, it is preferable according to an embodiment for the gray hair to be treated repeatedly, at intervals of one to several days, in particular 1 to 20 days, as described above with the agent described above. With this continuous repetition of the method the contact periods of about 2 to about 45 minutes, preferably about 5 to about 20 minutes, should be maintained.

In the case of test subjects with partly gray hair, it can be preferable to treat only the gray sections of the hair with the agent contemplated herein. To this end the test subject himself or a hairdresser uses an application aid, preferably in the form of a small brush or mascara brush. It is preferable here to choose the repeated application described above to gradually adjust the color.

Another embodiment also provides the use of an agent described above to intensify the color of colorings of keratin-containing fibers, in particular human hair, under induction by atmospheric oxygen.

The further embodiments also apply with necessary alterations to the use of the agents contemplated herein.

EXAMPLES

1. The Following Agents were Prepared (Amounts Given in wt. %)

TABLE 1

|  | E1 | E2 | E3 | C1 |
|---|---|---|---|---|
| Cetearyl alcohol | — | 2.0 | — | 9.5 |
| Cetyl alcohol | 0.49 | — | — | — |
| Coconut fatty alcohol | — | — | — | 2.4 |
| Ceteareth-12 | — | — | 1.0 | 0.5 |
| Ceteareth-20 | — | — | — | 0.5 |
| Laureth-2 | — | — | 2.0 | — |
| Sodium Laureth-6 Carboxylate | — | 0.5 | — | 2.1 |
| Sodium Myreth-3 Sulfate | — | — | — | 2.0 |
| Sodium Laureth-2 Sulfate | — | 0.68 | — | — |
| Lauryl Glucoside | — | — | — | 1.0 |
| 2-Octyldodecanol | — | — | — | 1.0 |
| Cetyl trimethylammonium chloride | 0.40 | — | — | — |
| L-Arginine | — | — | — | 0.6 |
| Isopropanol | 7.5 | — | — | — |
| 1,3-Butylene glycol | — | — | 10.0 | — |
| 1,2-Propylene glycol | — | — | 5.0 | — |
| 5,6-Dihydroxyindoline-HBr | 1.0 | 1.0 | 1.0 | 1.0 |
| Ascorbic acid | 0.5 | 0.5 | 0.5 | 0.2 |
| Methylparaben | 0.25 | — | — | — |
| Propylparaben | 0.25 | — | — | — |
| Sodium hydroxide | 0.98 | 0.58 | 0.8 | — |
| Ammonia | — | — | — | 0.6 |
| Perfume | | Qs | | |
| Water, demineralized | | to 100 | | |
| pH | 9.6 | 9.5 | 9.7 | 9.0 |

1.2 Application

The agents E1 to E3 were weighed into a pressure vessel (standard styling mousse can), the can was closed (clinched) and then a propellant gas mixture was added, consisting of 49% n-butane, 48% propane, 2% isobutane and 1% pentane in the weight ratio 89 g active ingredient solution:9 g propellant gas mixture.

The ready-to-use agents were applied to buffalo stomach hair in the liquor ratio 1 g of foam per 1 g of hair (agents E1 to E3) or 2 g of cream per 1 g of hair (agent C1) and left to act for a certain period. Then the agent was rinsed out of the hair and the hair was dried. The coloring process was then repeated if necessary.

The color intensity was then determined by colorimetry and ΔE (colored versus uncolored) was calculated. The ΔE value was calculated using the formula $\Delta E = \sqrt{(\Delta L)^2 + (\Delta a)^2 + (\Delta b)^2}$. The higher the ΔE value, the more intense the coloring.

2. Results 2.1 Single and Multiple Application

Table 2 shows the results following single and multiple applications of the coloring agents with a contact period of 20 minutes in each case.

TABLE 2

| Entry | Treatment | Applications | L | a | b | ΔE |
|---|---|---|---|---|---|---|
| #2.0 | Uncolored | — | 74.07 | 0.31 | 10.64 | |
| #2.1 | C1 | 1x | 58.53 | 1.66 | 9.71 | 15.6 |
| #2.2 | E1 | 1x | 34.14 | 2.04 | 4.08 | 40.5 |
| #2.3 | E2 | 1x | 55.18 | 1.56 | 6.08 | 19.5 |
| #2.4 | E3 | 1x | 51.96 | 1.01 | 5.18 | 22.8 |
| #2.5 | C1 | 4x | 38.95 | 2.79 | 5.93 | 35.5 |
| #2.6 | E1 | 4x | 21.62 | 1.24 | 2.57 | 53.1 |
| #2.7 | E2 | 4x | 35.80 | 1.18 | 3.45 | 39.0 |
| #2.8 | E3 | 4x | 28.66 | 1.37 | 1.89 | 46.3 |

It was found that after both a single application and multiple applications, the agents E1 to E3 lead to markedly more intense colorings of the hair. These results are also remarkable for the fact that less than half of the dye precursor amount of the comparative preparation is applied to the hair in the case of the agents contemplated herein (cf. liquor ratio 1.2).

A more intense coloring is obtained with agent E1 after a single application than with comparative agent C1 after four applications (Table 2, entries #2.2 and #2.5).

2.2 Period of Application

Table 3 shows the results following single and multiple applications of the coloring agents with varying contact periods.

TABLE 3

| Entry | Treatment | Contact period [min] | Applications | L | a | b | ΔE |
|---|---|---|---|---|---|---|---|
| #3.0 | uncolored | — | | 74.07 | 0.31 | 10.64 | |
| #3.1 | C1 | 20 | 1x | 58.53 | 1.66 | 9.71 | 15.6 |
| #3.2 | E1 | 5 | 1x | 43.45 | 2.11 | 5.96 | 31.0 |
| #3.3 | E1 | 20 | 1x | 34.14 | 2.04 | 4.08 | 40.5 |
| #3.4 | C1 | 20 | 4x | 38.95 | 2.79 | 5.93 | 35.5 |
| #3.5 | E1 | 5 | 4x | 24.35 | 1.69 | 3.45 | 50.3 |
| #3.6 | E1 | 20 | 4x | 21.62 | 1.24 | 2.57 | 53.1 |

A markedly better color result is obtained with agent E1 after a contact period of 5 minutes than with the comparative preparation after 20 minutes. This result is clear after a single application (Table 3, entries #3.1 and #3.2) and is still clearly discernible even after four applications with varying contact periods (Table 3, entries #3.4 and #3.5).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. An agent in foam form for coloring keratin-containing fibers, in particular human hair, under induction by atmospheric oxygen, the agent comprising, in a cosmetically acceptable carrier, at an alkaline pH of 8 to 10.5:

(a) as a color-forming component in the form of a dye precursor of a nature-analogous dye an indole and/or indoline derivative of formula (I),

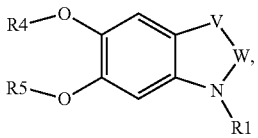

in which independently of one another
R¹ denotes hydrogen, a $C_1$-$C_4$ alkyl group or a $C_1$-$C_4$ hydroxyalkyl group,
V denotes $CHR^3$ and W denotes $CHR^2$, such that the bond between V and W corresponds to a single bond, or V denotes $CR^3$ and W denotes $CR^2$, such that the bond between V and W corresponds to a double bond, wherein in each case
—R² denotes hydrogen or a —COOH group, in which the —COOH group can also be present as a salt with a physiologically tolerable cation,
—R³ denotes hydrogen or a $C_1$-$C_4$ alkyl group,
R⁴ and R⁵ independently of one another denote hydrogen, a $C_1$-$C_4$ alkyl group or a —CO—R⁶ group, in which R⁶ denotes a $C_1$-$C_4$ alkyl group,
and/or one of the physiologically tolerable salts thereof with an organic or inorganic acid,
(b) an alkalizing agent,
(c) a propellant, and
(d) a fatty alcohol in an amount of from about 0.1 to about 1.5 wt. % based on the total weight of the agent;
wherein no additional oxidizing agent is included as a color-forming component.

2. The agent according to claim 1, wherein the indoline derivative of feature (a) is selected from derivatives of 5,6-dihydroxyindoline of formula (Ia)

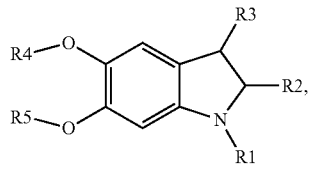

in which independently of one another
R¹ denotes hydrogen, a $C_1$-$C_4$ alkyl group or a $C_1$-$C_4$ hydroxyalkyl group,
R² denotes hydrogen or a —COOH group, in which the —COOH group can also be present as a salt with a physiologically tolerable cation,
R³ denotes hydrogen or a $C_1$-$C_4$ alkyl group,
R⁴ and R⁵ independently of one another denote hydrogen, a $C_1$-$C_4$ alkyl group or a —CO—R⁶ group, in which R⁶ denotes a $C_1$-$C_4$ alkyl group,
and/or one of the physiologically tolerable salts thereof with an organic or inorganic acid.

3. The agent according to claim 1, wherein the indoline derivative of feature (a) is chosen from 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and/or physiologically tolerable salts thereof with an organic or inorganic acid.

4. The agent according to claim 1, wherein the dye precursor of the nature-analogous dye (a) is included in an amount of from about 0.01 to about 10 wt.%, relative to a total weight of the agent.

5. The agent according to claim 4, wherein the dye precursor of the nature-analogous dye (a) is included in the amount of from about 0.1 to about 2.0 wt.%, relative to the total weight of the agent.

6. The agent according to claim 5, wherein the dye precursor of the nature-analogous dye (a) is included in the amount of from about 0.6 to about 1.2 wt.%, relative to the total weight of the agent.

7. The agent according to claim 1, wherein the propellant (c) is chosen from propane, n-butane, i-butane, pentane or mixtures of these compounds.

8. The agent according to claim 1, wherein the agent comprises as the alkalizing agent (b) an inorganic alkalizing agent chosen from sodium hydroxide, potassium hydroxide, sodium carbonate, or potassium carbonate.

9. The agent according to claim 1, further comprising the fatty alcohol in the amount from about 0.2 to about 1.5 wt.%, relative to the total weight of the agent.

10. The agent according to claim 1, further comprising a surfactant in an amount from about 0.1 to about 5 wt.%, relative to a total weight of the agent.

11. The agent according to claim 10, further comprising the surfactant in the amount from about 0.2 to about 3 wt.%, relative to the total weight of the agent.

12. The agent according to claim 1, wherein the agent has a pH in a range of about 8.8 to about 10.5.

13. The agent according to claim 12, wherein the agent has a pH in the range of about 9.4 to 9.9.

14. A method for coloring keratin-containing fibers, the method comprising the steps of:
applying an agent to the keratin-containing fibers, the agent comprising, in a cosmetically acceptable carrier, at an alkaline pH of 8 to 10.5:
(a) as a color-forming component in a form of a dye precursor of a nature-analogous dye an indole and/or indoline derivative of formula (I),

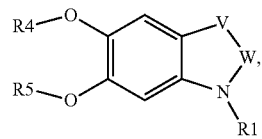

in which independently of one another
R¹ denotes hydrogen, a $C_1$-$C_4$ alkyl group or a $C_1$-$C_4$ hydroxyalkyl group,
V denotes $CHR^3$ and W denotes $CHR^2$, such that the bond between V and W corresponds to a single bond,
or V denotes $CR^3$ and W denotes $CR^2$, such that the bond between V and W corresponds to a double bond, wherein in each case
—R² denotes hydrogen or a —COOH group, in which the —COOH group can also be present as a salt with a physiologically tolerable cation,
—R³ denotes hydrogen or a $C_1$-$C_4$ alkyl group,
R⁴ and R⁵ independently of one another denote hydrogen, a $C_1$-$C_4$ alkyl group or a —CO—R⁶ group, in which R⁶ denotes a $C_1$-$C_4$ alkyl group,
and/or one of the physiologically tolerable salts thereof with an organic or inorganic acid,
(b) an alkalizing agent,
(c) a propellant, and
(d) a fatty alcohol in an amount of from about 0.1 to about 1.5 wt. % based on the total weight of the agent;

wherein no additional oxidizing agent is included for the color-forming components;

allowing the agent to remain on the keratin-containing fibers for a contact period; and rinsing the agent from the keratin-containing fibers after the contact period.

15. The method according to claim 14, wherein allowing comprises allowing the agent to remain on the keratin-containing fibers for a contact periof of from about 2 to about 45 minutes.

16. The method according to claim 14, wherein applying the agent comprises applying the agent comprising the indoline derivative of feature (a) chosen from 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and/or physiologically tolerable salts thereof with an organic or inorganic acid.

17. The method according to claim 14, wherein applying the agent comprises applying the agent comprising the dye precursor of the nature-analogous dye (a) present in an amount of from about 0.01 to about 10 wt.%, relative to a total weight of the agent.

18. The method according to claim 14, wherein applying the agent to the keratin-containing fibers comprises applying the agent to human hair.

* * * * *